US008664963B2

(12) United States Patent
Reese et al.

(10) Patent No.: US 8,664,963 B2
(45) Date of Patent: Mar. 4, 2014

(54) TEST DEVICE FOR MEASURING PERMEABILITY OF A BARRIER MATERIAL

(75) Inventors: Matthew Reese, Golden, CO (US); Arrelaine Dameron, Boulder, CO (US); Michael Kempe, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 280 days.

(21) Appl. No.: 12/842,770

(22) Filed: Jul. 23, 2010

(65) Prior Publication Data

US 2011/0018563 A1 Jan. 27, 2011

Related U.S. Application Data

(60) Provisional application No. 61/228,244, filed on Jul. 24, 2009.

(51) Int. Cl.
*G01R 27/08* (2006.01)

(52) U.S. Cl.
USPC ............ 324/693; 324/694; 324/715; 324/719

(58) Field of Classification Search
USPC .................. 324/693, 694, 715, 719
See application file for complete search history.

(56) References Cited

U.S. PATENT DOCUMENTS

| 2,932,592 | A | * | 4/1960 | Cameron | ............ | 359/589 |
|---|---|---|---|---|---|---|
| 4,050,995 | A | | 9/1977 | Bredeweg | | |
| 6,804,989 | B2 | | 10/2004 | Bujas et al. | | |
| 7,178,384 | B2 | | 2/2007 | Bujas et al. | | |
| 7,257,990 | B2 | | 8/2007 | Bujas et al. | | |
| 7,371,563 | B2 | * | 5/2008 | Duffy et al. | ................ | 435/288.5 |
| 7,599,192 | B2 | * | 10/2009 | Pennaz et al. | ................ | 361/761 |
| 2005/0130823 | A1 | * | 6/2005 | Budd | ................ | 501/5 |
| 2007/0032972 | A1 | * | 2/2007 | Glover et al. | ................ | 702/77 |
| 2007/0292957 | A1 | * | 12/2007 | Chua et al. | ................ | 436/5 |
| 2007/0299385 | A1 | * | 12/2007 | Santini et al. | ................ | 604/19 |
| 2008/0297169 | A1 | * | 12/2008 | Greenquist et al. | ........... | 324/600 |
| 2009/0151107 | A1 | * | 6/2009 | Shank et al. | ............... | 15/250.05 |
| 2010/0025238 | A1 | * | 2/2010 | Gottlieb et al. | ............... | 204/401 |

FOREIGN PATENT DOCUMENTS

WO WO 2008082362 A1 * 7/2008

OTHER PUBLICATIONS

U.S. Appl. No. 61/119,200, filed Dec. 2008, Graham et al.*
P. F. Carcia, R. S. McLean, M. D. Groner et al., "Gas diffusion ultrabarriers on polymer substrates using Al[sub 2]O [sub 3] atomic layer deposition and SiN plasma-enhanced chemical vapor deposition," Journal of Applied Physics, vol. 106, No. 2, pp. 023533, 2009.
G. L. Graff, R. E. Williford, and P. E. Burrows, "Mechanisms of vapor permeation through multilayer barrier films: Lag time versus equilibrium permeation," Journal of Applied Physics, vol. 96, No. 4, pp. 1840-1849, 2004.

(Continued)

*Primary Examiner* — Jermele M Hollington
*Assistant Examiner* — Temilade S Rhodes-Vivour
(74) *Attorney, Agent, or Firm* — Paul J. White

(57) ABSTRACT

A test device for measuring permeability of a barrier material. An exemplary device comprises a test card having a thin-film conductor-pattern formed thereon and an edge seal which seals the test card to the barrier material. Another exemplary embodiment is an electrical calcium test device comprising: a test card an impermeable spacer, an edge seal which seals the test card to the spacer and an edge seal which seals the spacer to the barrier material.

21 Claims, 7 Drawing Sheets

(56) References Cited

OTHER PUBLICATIONS

M. S. Weaver, L. A. Michalski, K. Rajan et al., "Organic light-emitting devices with extended operating lifetimes on plastic substrates," Applied Physics Letters, vol. 81, No. 16, pp. 2929-2931, 2002.

M. D. Kempe, "Modeling of rates of moisture ingress into photovoltaic modules," Solar Energy Materials and Solar Cells, vol. 90, No. 16, pp. 2720-2738, 2006.

D. J. Coyle, H. A. Blaydes, J. E. Pickett et al., "Degradation kinetics of CIGS solar cells," Proceedings of the 2009 34th IEEE Photovoltaic Specialists Conference (PVSC 2009), pp. 001943-001947, 2009.

J. H. Choi, Y. M. Kim, Y. W. Park et al., "Evaluation of gas permeation barrier properties using electrical measurements of calcium degradation," Review of Scientific Instruments, vol. 78, No. 6, pp. 064701, 2007.

R. Paetzold, A. Winnacker, D. Henseler et al., "Permeation rate measurements by electrical analysis of calcium corrosion," Review of Scientific Instruments, vol. 74, No. 12, pp. 5147-5150, Dec. 2003.

H. J. Svec, and C. Apel, "Metal-Water Reactions," Journal of the Electrochemical Society, vol. 104, No. 6, pp. 346-349, 1957.

A. Dameron, M. Reese., T. Moricone and M. Kempe, "Understanding moisture ingress and packaging requirements for photvoltaic modules", Photolvoltaics International, 5, 121 (2009).

Nissen, D.S., "Low-Temperature Oxidation of Calcium by Water-Vapor," Oxidation of Metal, vol. 11, No. 5, pp. 241-261 (1977).

Greg, S. J., et al., "The Oxidation of Calcium in Moist Oxygen," Journal of the Chemical Society, pp. 884-888 (1961).

Nisato, G., et al., "Evaluating High Performance Diffusion Barriers: the Calcium Test," Asia Display IDW02 1435 (2001).

Paul, D.R & Kemp, D.R., "The diffusion time lag in polymer membranes containing adsorptive fillers," J. Polym Sci Symp, 41, pp. 79-93 (1973).

Paul, D.R., "Effect of immobilizing adsorption on the diffusion time lag," J. of Polymer Science, Part A-2, 7, pp. 1811-1818 (1969).

\* cited by examiner

US 8,664,963 B2

TEST DEVICE FOR MEASURING PERMEABILITY OF A BARRIER MATERIAL

CROSS-REFERENCE TO RELATED APPLICATIONS

This application claims the benefit of U.S. Provisional Application No. 61/228,244 filed Jul. 24, 2009, which is incorporated herein by reference in its entirety.

CONTRACTUAL ORIGIN

The United States Government has rights in this invention under Contract No. DE-AC36-08GO28308 between the United States Department of Energy and the Alliance for Sustainable Energy, LLC, the Manager and Operator of the National Renewable Energy Laboratory.

TECHNICAL FIELD

The described subject matter relates generally to test devices for measuring permeability of a barrier material.

BACKGROUND

Oxygen and moisture barriers are commonly used for packaging components in a wide variety of industries, e.g., ranging from food packaging to electronics. The requirements vary significantly for permeation, cost, flexibility, weight, and transparency, among other considerations. Organic light emitting diodes (OLEDs) and flexible photovoltaics (PV) have some of the most demanding specifications for water vapor barriers, needing to couple low permeation rates with good flexibility and transparency.

For PV in general, low cost and scalability are important factors. Also PV is often subject to temperature fluctuations and harsh weather conditions, in addition to the expected ultraviolet (UV) exposure. Presently, to meet warranty specifications, glass and metal foil barriers are commonly used. However, these barriers may be heavy, expensive, and/or are not readily used for roll-to-roll manufacturing processes (metal foil barriers cannot be the front-sheet in roll-to-roll manufacturing). For weight reasons as well as benefits in cost and scalability through roll-to-roll manufacturing processes, a transparent, flexible barrier that can supplant existing approaches (e.g. glass superstrates) is highly desired by the PV industry.

More specifically, OLEDs and organic photovoltaics need to be packaged using a material with a low water vapor transmission rate (WVTR), in some cases on the order of $10^{-6}$ to $10^{-8}$ g/m$^2$/day. For other PV applications, materials are generally not considered to have meaningful barrier properties unless their WVTR is at least about $10^{-4}$ g/m$^2$/day, and more desirably at least about $10^{-6}$ g/m$^2$/day.

The WVTR numbers typically quoted are at ambient temperatures or 38° C. In PV applications, damp heat conditions of 85° C. at 85% relative humidity (RH) are typically used in qualification tests, such as IEC (International Electrochemical Commission) 61646 and IEC 61215. Such conditions significantly increase permeation rates of the barriers and may irreversibly damage expensive structures. Therefore, it is often desired to be able to separately test individual barriers under a variety of environmental conditions.

Several techniques have been developed for measuring WVTRs of barrier materials below $10^{-4}$ g/m$^2$/day, however, no generally accepted test standard exists. Of the experimental techniques with ultra-low sensitivities, the electrical calcium test offers high throughput capabilities, easily controlled environmental conditions, and in-situ measurements capable of studying steady state WVTRs and transients. The calcium degradation test method uses a thin calcium (Ca) layer to scavenge water that passes through a test barrier. Determining the amount of Ca degradation depends on the absorption of nearby water molecules by the Ca metal film to form CaO or Ca(OH)$_2$. The electronic detection method is based on the transition of the Ca film from a highly conductive metal to a non-conductive oxidized state. The amount of Ca remaining can be calculated from the resistance measurements (using an assumed or a measured bulk resistivity for Ca), and the WVTR can be calculated from the rate of change in conductance with time. To aid in the research and development of such barriers, a high-throughput, electrical calcium method that can measure many barriers in parallel under a variety of test conditions (high temperature and relative humidity) with high accuracy is desirable.

Another limitation in measuring permeability using the electrical calcium test is the need for a better edge seal. Universally, in Ca electrical testing to date, a UV curable epoxy is used as a sealant for the edge seal. Numerous epoxies and other adhesives deleteriously interact with the calcium to varying degrees. While outgassing is possible for certain adhesives, great care needs to be taken not to harden them prematurely. Furthermore, UV curable adhesives are found to sometimes not be fully cured or when fully cured to become brittle, thereby increasing the chance of delamination. When measured at elevated temperatures, thermal expansion further increases the risk of delamination in epoxies. Furthermore, in the best epoxy edge seals, while edge permeation relative to many material systems is low, the ability to make extremely long-lived measurements is limited. Typically, only about 200-300 hr of permeability testing at about 38° C./90% RH (relative humidity) is achievable due to poor availability of good edge seals.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments describe an electrical calcium test device comprising a thin-film conductor-patterned sensor test card (substrate coated with conductor pattern such as metal, FTO or ITO), edge spacer, barrier film (under test) and edge seal for accurately measuring the permeation of water through films of barrier materials and any resultant degradation of the barrier material. Embodiments are disclosed for the test device wherein a thin film pattern of Ca sensor metal is deposited (e.g., by evaporation or sputtering) onto an impermeable substrate (e.g., glass). The pattern is composed of multiple Ca sensors that are connected to patterned inert electrical conductor lines in a four wire resistance measurement configuration. One Ca (or other metals or other organic or organometallic compound) that can be readily oxidized by water) sensor is used as a witness to monitor the integrity of the edge seal with respect to failure. The noncorrosive inert electrically conductive lines (e.g., Pt, Au, fluorine doped $SnO_2$, etc.) are deposited onto (or underneath) the Ca film so that the resistance of the Ca sensors can be measured in either a two- or four-point configuration. The inert contacts are configured to be passed through an edge seal to the outside of the device. A water impermeable spacer that surrounds the Ca patterned measurement area is then sandwiched between the patterned glass (metal with insulating coating, etc.) substrate and the barrier film. The edges of the sandwich are sealed (e.g., under compression if desired) using an edge seal material with low permeability to water. The spacer shape and dimensions which define the volume of the space between the barrier film and patterned substrate (test card) are configured to accommodate the measurement of either high, medium, or low permeability barrier materials. The device may include an optional temperature sensing device (e.g., thermocouple, thermistor, or resistance temperature detector). The structure is considered semi-hermetic with respect to the test barrier's permeation so that on the timescale of a test the only avenue of water transport to the Ca film is through the barrier film. The other path of moisture transport is through the edge seal. This is documented by the witness line.

Exemplary embodiments disclose that the entire test device is placed in a controlled environment chamber, where the amount of oxidized Ca present (or alternatively, the amount of Ca missing) is detected by electrical means. The electronic detection method depends on the transition of the Ca film from a highly conductive metal to a non-conductive oxide. The amount of Ca remaining can be calculated from resistance measurements (using an assumed or a measured bulk resistivity for Ca), and the WVTR can be calculated from the rate of change in conductance with time. Upon manipulation and analyses of resistance data, the test device offers highly quantitative results. Degradation of the edge seal (and consequent termination of the measurement of the barrier film is monitored by electrical resistance measurements as well. In using the test device under various environmental conditions, the electrical calcium test device displays excellent sensitivity for measuring steady state WTVRs ($10^{-6}$ g/m²/day) as well as transients to determine breakthrough and lag times of barrier materials.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

Briefly, an electrical calcium test device is disclosed for measuring the permeation of water through films of barrier materials. The device improves accuracy, throughput, reproducibility, and longevity of testing. Exemplary embodiments describe a device comprising a thin-film patterned sensor test card (e.g., substrate coated with metal or other conductive or semi-conductive pattern), edge spacer, barrier film (under test) and edge seal for accurately measuring steady state WTVRs (about $10^{-6}$ g/m²/day), as well as transients to determine breakthrough and lag times of barrier materials and any resultant degradation of the barrier material. Embodiments are disclosed for the test device wherein a thin film pattern of calcium (Ca) sensor metal is deposited (e.g., by evaporation or sputtering) onto an impermeable substrate (e.g., glass). The pattern is composed of multiple Ca sensors that are connected to patterned inert electrical contacts in a two or four wire resistance measurement configuration.

Exemplary embodiments include one Ca sensor used as a witness to monitor the integrity of the edge seal with respect to failure and quality of sample assembly. The noncorrosive inert metal lines (e.g., Pt, Au, F:$SnO_2$, etc.) are deposited to contact (e.g., onto or underneath) the Ca film so that the resistance of the film can be measured in multiple configurations (e.g., a two- or four-wire configuration). The inert metal contacts are configured to be passed through an edge seal to the outside of the device. A water impermeable spacer is provided adjacent (e.g., surrounding) the Ca patterned measurement area between the patterned glass substrate and the barrier film. The edges are sealed (e.g., under compression) using an edge seal material with low permeability to water. The spacer shape and dimensions define a volume of space between the barrier film and the patterned substrate (also referred to as the test card), and is configured to accommodate the measurement of different (e.g., high, medium, and low) permeability barrier materials. The device may also include a temperature sensing device (e.g., a thermocouple, thermistor, or resistance temperature detector). The structure may be semi-hermetic with respect to the test barrier's permeation, on the timescale of a measurement, so that water transport to the Ca sensor is primarily through the barrier film.

Exemplary embodiments of the test device, and methods of production thereof, may be better understood with reference to the Figures and following discussion.

Figure 1:
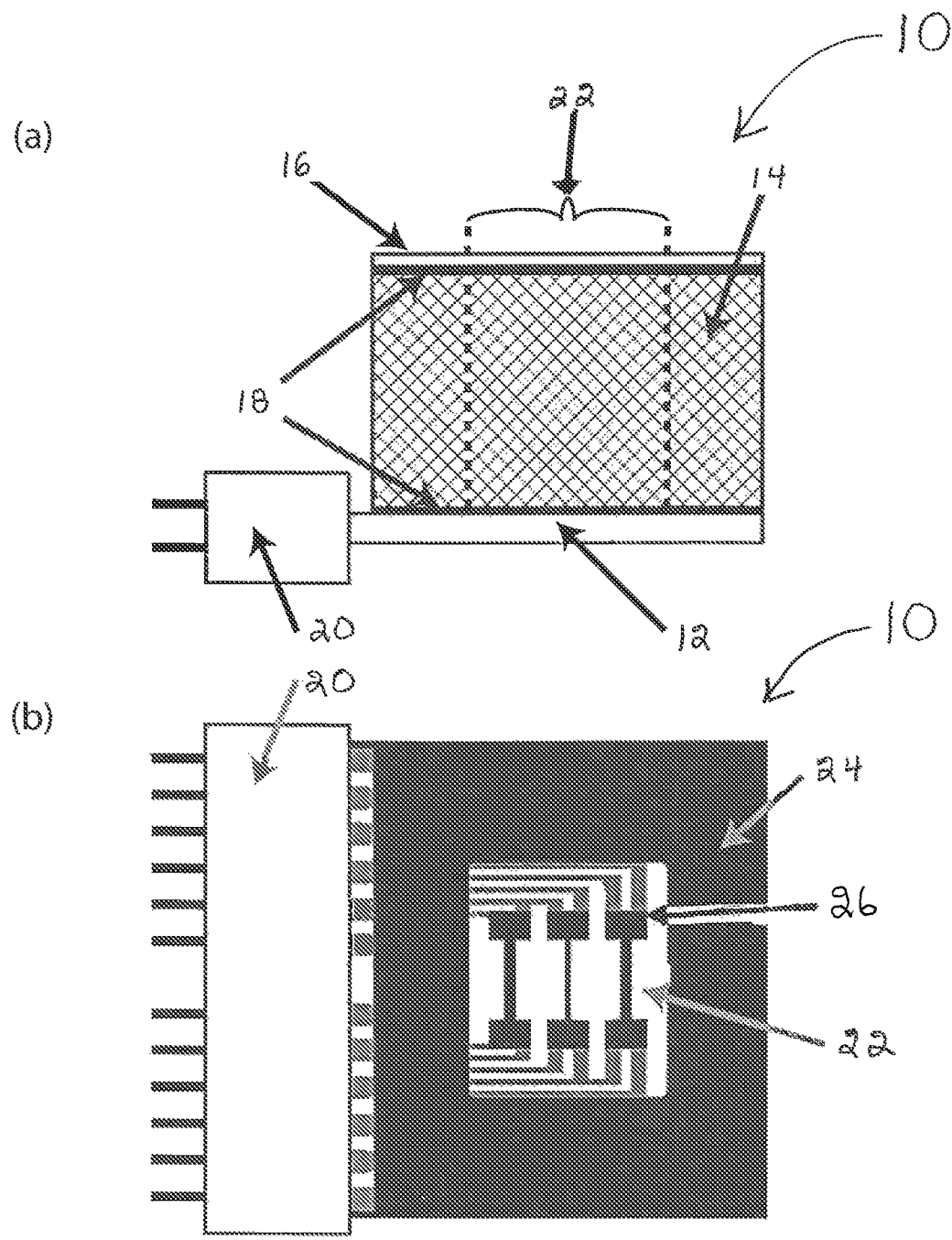
FIG. 1 is a structural diagram of an exemplary barrier testing device for an electrical calcium test, wherein (a) is a side view, and (b) is a top view.

FIG. 1 is a structural diagram of an exemplary barrier testing device 10 for an electrical calcium test showing the main components: test card 12 (or conductor patterned substrate), spacer 14, barrier film 16 (under test), and edge seal 18 as well as electrical connector 20: (a) side view, (b) top view. The spacer 14 in FIG. 1 (a) is shown in a cross hatched pattern for purposes of clear illustration. The barrier film 16 is depicted as a transparent material in FIG. 1 to illustrate the measurement area 22 of the barrier 16 and for viewing the metal pattern deposited on the test card 12 in FIG. 1(b). The combined edge seal/spacer 24 in FIG. 1b defines the measurement area 22 of the barrier film as well as the measurement area of the metal patterned substrate 12. The dashed lines in the spacer of FIG. 1 (a) show the position of the hidden interior walls of the spacer 14 which also define the measurement area 22 of the barrier 16 and test card 12. A water impermeable spacer 14 (e.g., metal, glass, ceramic) is provided adjacent the Ca patterned measurement area between the patterned glass substrate 12 and the barrier film 16. The edges are sealed using an edge seal material having low permeability to water. Edge seal areas 24 may encompass the top surface and bottom surface area of the spacer which mate to the barrier film 16 and patterned substrate 12 respectively. The spacer shape and dimensions which define the volume of the space between the barrier film and patterned substrate (or "test card") may be configured and dimensioned to accommodate the accurate measurement of different (e.g., high, medium, and low) permeability barrier materials. A Ca/inert conductor thin-film line pattern (viewable through the transparent barrier layer 16 in FIG. 1(b)) is provided on a top surface of the substrate facing the barrier layer 16, and is extended underneath the edge seal area 24 to mate with an electrical connector 20.

Figure 2:
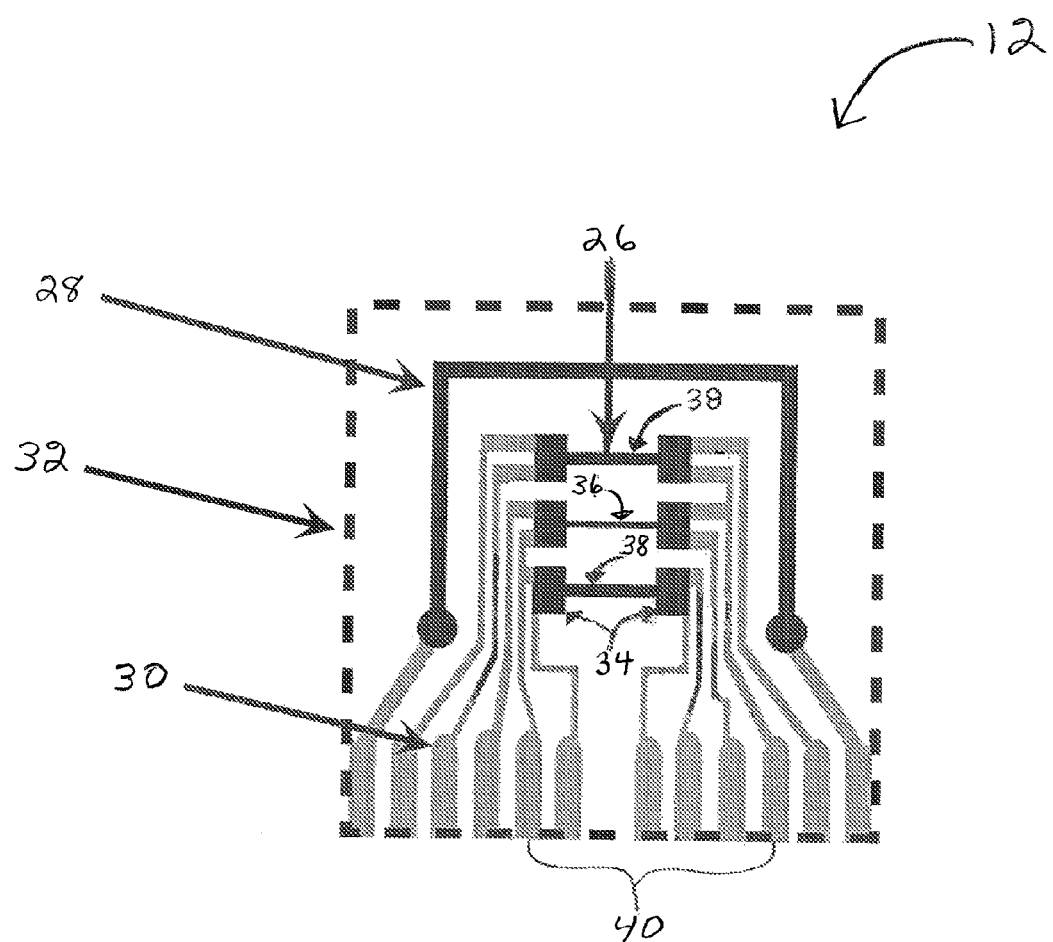
FIG. 2 is a top-view structural diagram of an exemplary test card showing patterned calcium sensors, a calcium witness line, and inert electrically conductive lines deposited on a substrate.

FIG. 2 is a top-view schematic drawing of an exemplary test card 12 showing the patterned Ca sensors 26, Ca witness line 28, and inert electrically conductive lines 30 deposited on a low-outgassing, electrically insulating, water-impermeable substrate 32 (e.g., glass). The Ca witness line 28 serves as a sensor as well. The dumbbell-shaped Ca sensors 26 may be provided with enlarged contact pads 34 to better contact the electrically conductive lines. In an exemplary embodiment, the enlarged pads 34 at each end of the calcium sensor lines 36 and 38 contact two electrically-conducting lines 30 for four wire-type resistance measurements. The electrically conductive lines 30 may be composed of materials of inert nature, such as, but not limited to, platinum (Pt), gold (Au), to name a few examples. Alternatively, in some embodiments an inert metal oxide may be used as the electrical conductor (e.g., fluorine doped tin oxide).

Multiple Ca sensor lines enable multiple measurements of the WVTR. Occasionally a Ca sensor line may be bad or a contact may be non-functional. Accordingly, providing this redundancy generally enables such instances to still be salvaged, and further guards against spurious results from poor construction.

The width to length ratio of the Ca test lines can be adjusted to maximize the sensitivity of a chosen range for the resistance measurement. Examples of two different width to length ratios for the Ca sensors are shown in FIG. 2 (e.g., the center Ca sensor line 36 is thinner than the two outer Ca sensor lines 38). Other embodiments of width to length ratio of the Ca sensor lines are envisioned and are not limited to arrangements shown. A 4-wire measurement may be employed to reduce or altogether eliminate the effects of contact resistance. In other embodiments, however, a 2-wire measurement may be employed. To maximize space on the test card, one or more of the electrically conductive lines 40 may be bifurcated to share contacts 40 with two different Ca sensors for making 4-wire measurements, e.g., as shown in FIG. 2.

To maximize sensitivity, the area of the Ca sensors may be minimized. Increased sensitivity results from a single small area Ca trace with a high length to width ratio. For most barrier technologies the reduction in sensitivity does not impact the utility of the test. Instead, redundancy and averaging of multiple traces increases measurement accuracy and reliability.

Another feature of the patterned test card is the integration of a witness line into the test structure (e.g., as shown in FIG. 2) to monitor the integrity of the edge seal. Any degradation or moisture ingress through the edge seal is monitored by electrical resistance measurements of the witness line.

Figure 3:
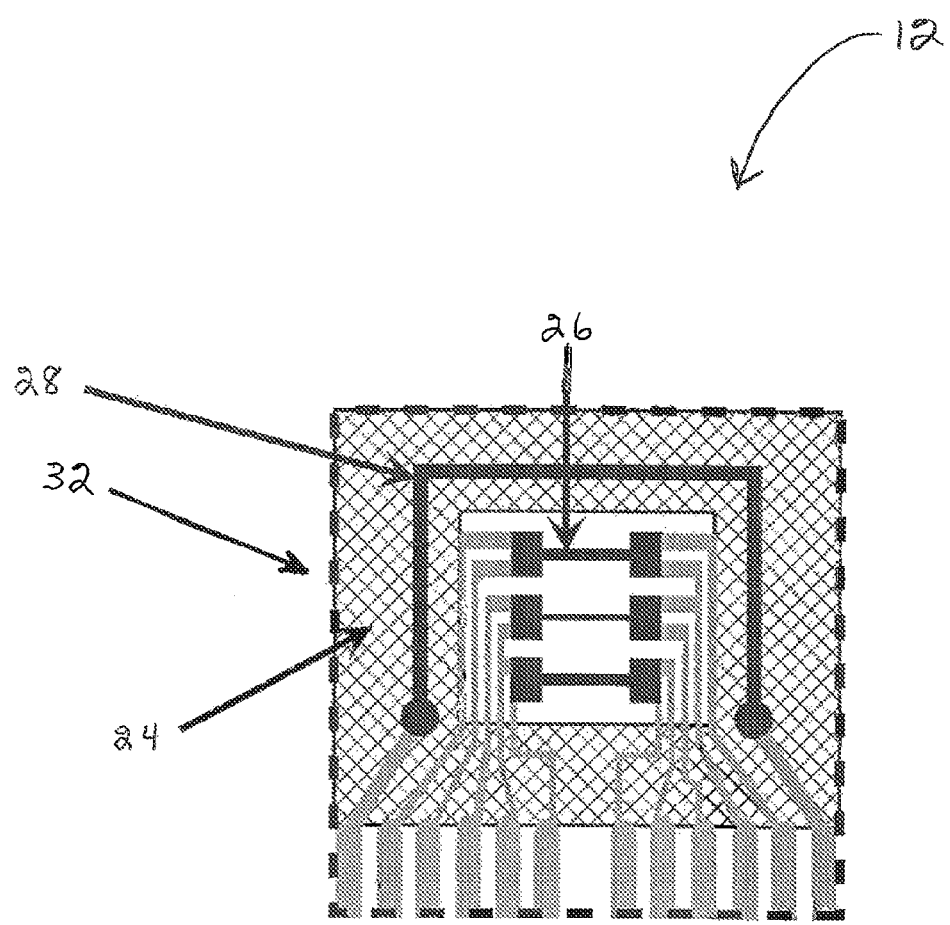
FIG. 3 is a top-view structural diagram of a test card showing a calcium witness line and calcium sensors in relation to the edge seal and spacer position.

FIG. 3 is a top-view schematic drawing of a test card 12 showing a Ca witness line 28 and Ca sensors 26 deposited on a substrate 32 in relation to the edge seal/spacer position 24 after fabrication of the test device. The Ca witness line 28 is positioned on the sensor card in direct contact with the edge seal. The test may be limited by the edge seal, and any failure (e.g., due to poor outgassing or a very long test) can allow moisture ingress through the edge seal, which can be electrically detected by the witness line. The witness line also serves as a partial baseline of test sensitivity. Any changes in the witness line (e.g., during early stages), may be due to mechanisms other than moisture ingress. To use the witness line as a more accurate measure of background effects, it may be implemented in a four-wire configuration. For gross monitoring of edge seal failures, the witness line may be measured in a 2-wire configuration (e.g., as shown in FIGS. 2 and 3).

Figure 4:
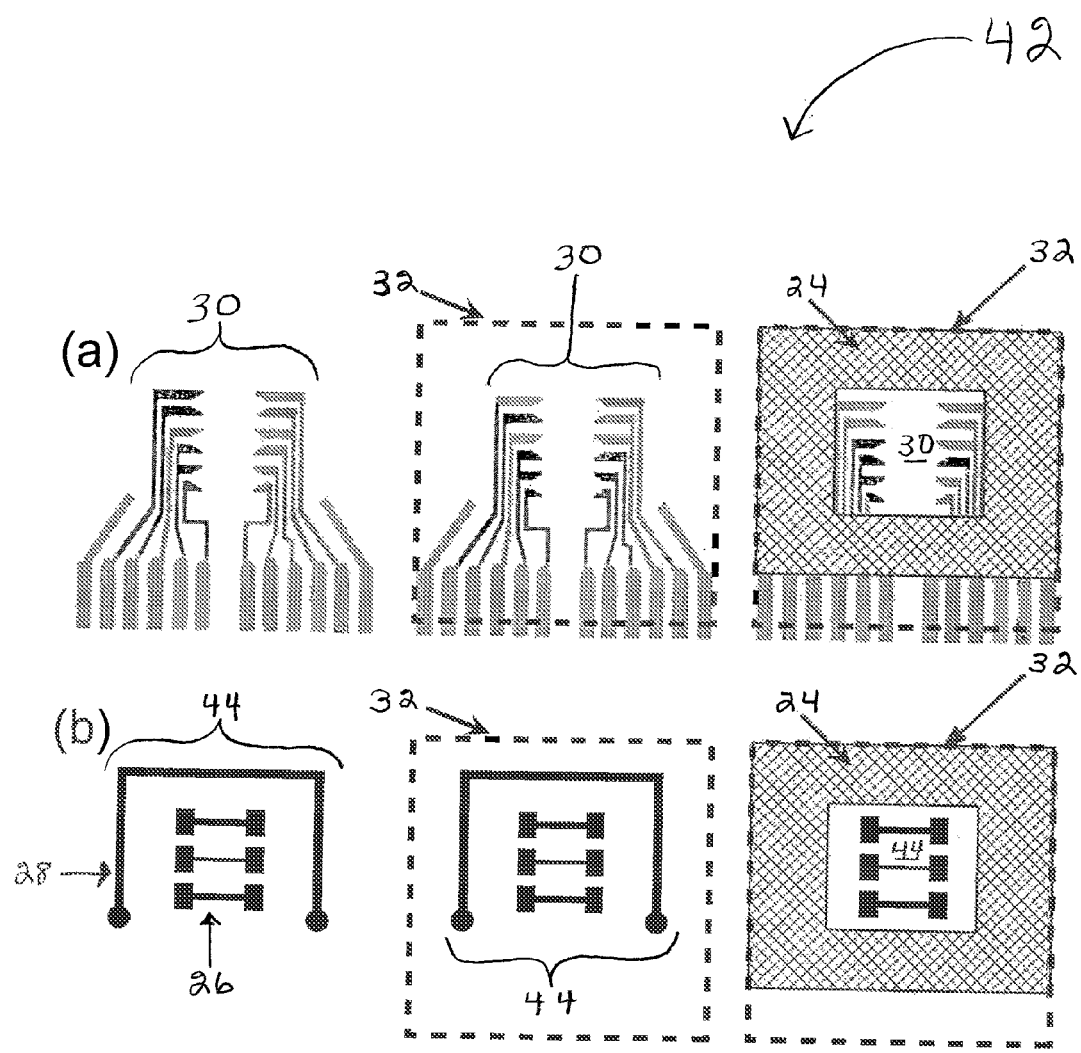
FIG. 4 show exemplary shadow mask patterns for depositing (a) an inert electrical conductor line pattern, and (b) a calcium sensor and witness line metal pattern.

Patterned Ca and metal lines may be deposited (e.g., sputtering or evaporation) through a shadow mask. FIG. 4 is a structural diagram of the exemplary shadow mask patterns 42 for depositing (a) the inert metal electrically conductive line shadow mask pattern 30 and (b) the Ca sensor and witness line shadow mask pattern 44 for an exemplary 2 inch-square substrate. Substrate 12 and edge seal/spacer positions 24 are outlined to show eventual test device configuration.

Figure 5:
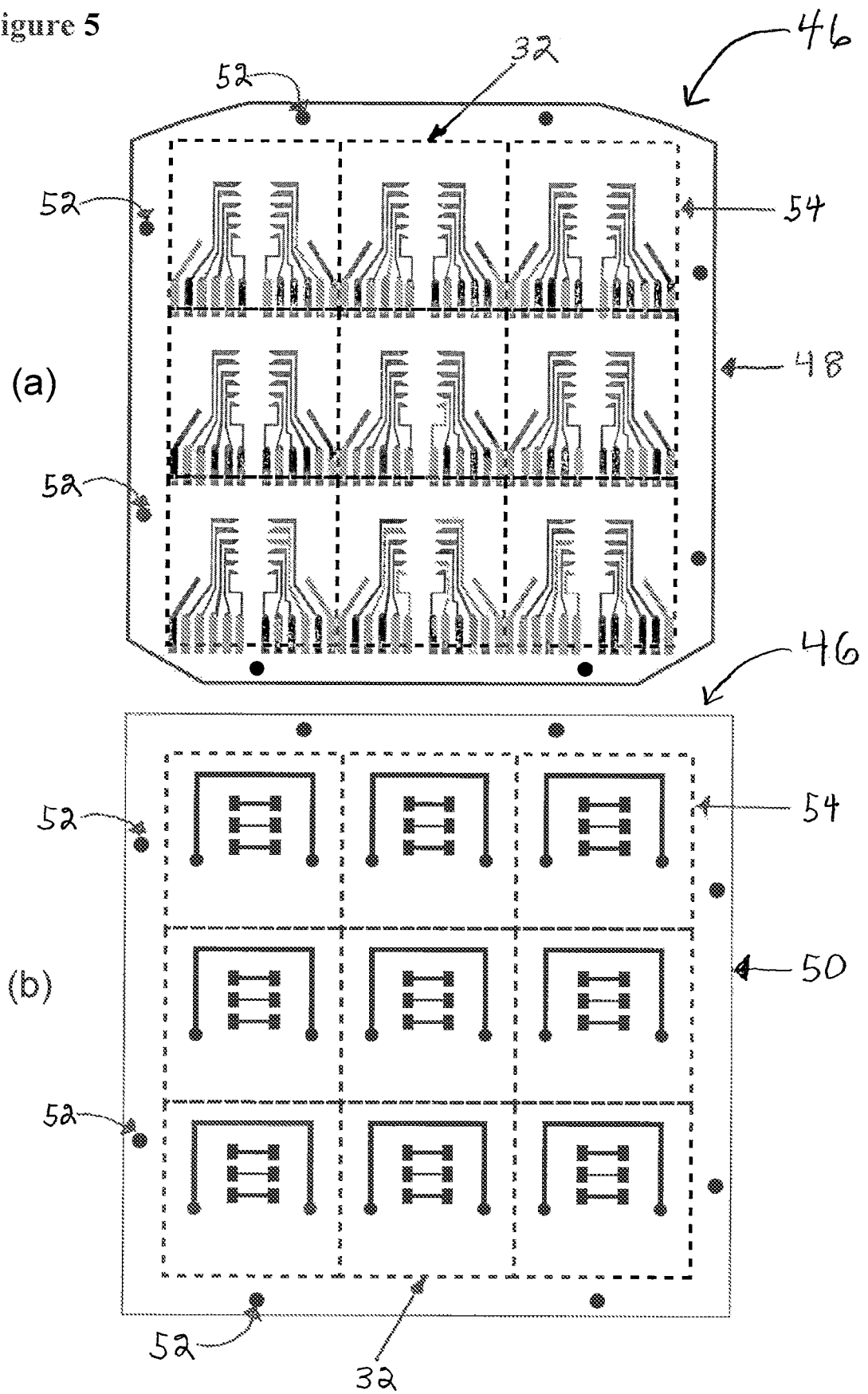
FIG. 5 show exemplary shadow mask patterns for depositing onto a six inch square substrate to produce nine separate two inch square patterned test cards, wherein: (a) is an inert electrical conductor line pattern, and (b) is a calcium sensor and witness line metal pattern.

For increased throughput (e.g., during a manufacture process), many patterned test cards can be fabricated onto a larger single substrate using shadow mask techniques. FIG. 5 is a structural diagram of exemplary shadow mask patterns 46 for depositing onto a 6 inch square substrate to produce nine separate 2 inch-square patterned test cards upon scribing the substrate at the dashed lines: (a) inert electrical conductor line pattern 48, (b) Ca sensor and witness line metal pattern 50. Set screws in the mask holder (shown in FIG. 5 as darkened circles surrounding the periphery of each shadow mask) are used to align the same edges between the inert electrical conductor and Ca depositions, thereby helping to reduce alignment errors. It is noted that the dark circles shown in the figure are alignment pins for the masks. The set screws are not shown in the image. Nine two inch spare substrates 54 to be diced from the deposited pattern are shown by dashed lines 54. The substrates may be diced across the terminals of the inert electrical conductor pattern in order to precisely terminate the electrical conductor at the edge of the substrate and help make a good connection to the electrical connector shown in FIG. 1. Other alignment techniques now known or later developed may also be used to establish pattern registration. Samples may be diced after subsequent depositions of Ca and inert metal.

As the test card is designed for measurements of resistance, small thermal fluctuations may cause inaccurate measurements. For this purpose, the use of temperature measurement devices may be readily integrated into the structure of the test device. Such a detector may be incorporated into the interior of the device (with electrical leads passed through the edge seal to the outside), attached to the device (e.g., on the outside housing of the device), or be provided altogether separate from the device. Particular design considerations may include the ambient environment where the device is being used because there may be significant changes in the calcium resistance as well as Arrhenius behavior of barriers in some test conditions. In ambient conditions, temperature fluctuations of 5° C. or more are common over the course of a single day.

Figure 6:
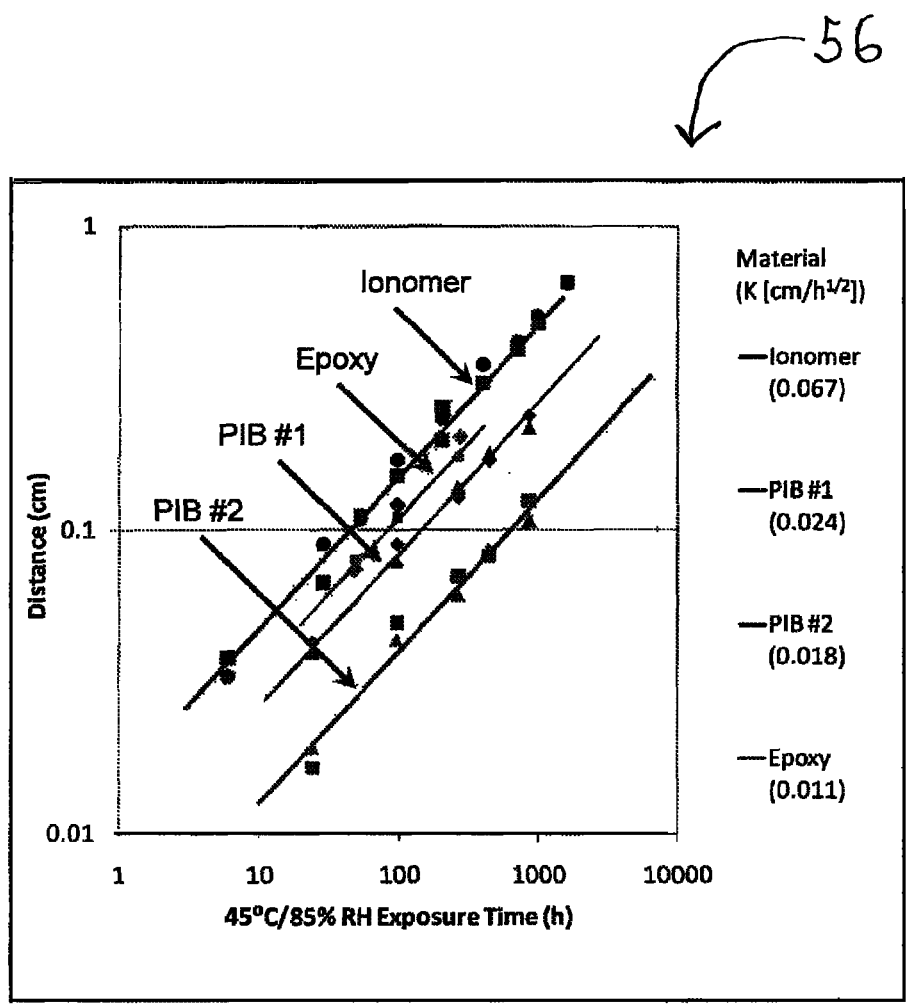
FIG. 6 is a graph showing moisture ingress distance through various edge seal materials versus time when exposed to a 45° C. and 85% RH environment.

Measurements of breakthrough time of a series of adhesive materials showed poly-isobutylene (PIB)-based materials filled with a desiccant (e.g., HelioSeal PVS-101-S commercially available from ADCO Products, Inc.) to have significantly lower permeation than other materials. FIG. 6 is a graph 56 of the moisture ingress distance through various edge seal materials vs time when exposed to a 45 C and 85% RH environment. FIG. 6 shows that desiccant filled PIB (polyisobutylene) adhesive materials (sample PIB #1 and sample PIB #2) have significantly enhanced resistance to water permeation, e.g., when compared to epoxy and ionomer type edges seal materials. Sample PIB #2 is 4 times better than the best measured UV epoxy.

With constant temperature, the time scale for a one dimensional, diffusion controlled process for water permeation scales as the square of the characteristic distance, X, such according to equation 1, below:

$$X=K\sqrt{t} \quad \text{(Eqn. 1)}$$

Where K is a proportionality constant related to a specific material's permeability, and t is time. In FIG. 6, the constant K is expressed as $cm/hr^{1/2}$. Thus, FIG. 6 shows that for equivalent minimum measurement times, an edge seal made of UV epoxy must be approximately 16 times wider than one made of PIB filled dessicant material. Additionally such edge seals using PIB material are also more flexible and have better adhesion. The desiccant-filled PIB edge seal material demonstrates verified stability with regards to interaction with calcium and can be readily dried of any residual water vapor. A narrow (e.g., 10 mm wide) PIB-based edge seal has been demonstrated to allow thousands of hours of successful barrier testing at 85° C. and 85% RH.

A spacer is readily integrated into the device allowing multiple advantages. Spacers made of a highly impermeable material (e.g., metal, glass, ceramic, or combination) can be used to reduce the effect of defects (e.g., so-called "pinholes") in the barrier film under test to allow an average WVTR to be measured. This is accomplished by increasing the distance between the barrier and the patterned test card. In addition, test accuracy can be improved if each component is first outgassed. If the spacer is assembled with the edge seal material, then both can be outgassed at higher temperatures to drive off moisture more quickly. In one example, it was found that both aluminum and fused silica spacers when outgassed properly (e.g., about 30-60 min. 300° C. bake, followed by an overnight bake at 140° C. with the edge seal material—both in an inert atmosphere environment) performed similarly, showing that residual moisture was not adsorbed/absorbed by the spacer. Shorter and lower temperature procedures may also be used. No outgassing procedure, however, typically results in oxidation of the Ca sensor without any moisture transport through the barrier under test. This has been demonstrated by fully assembling a sample and leaving it in an inert environment overnight.

Figure 7:
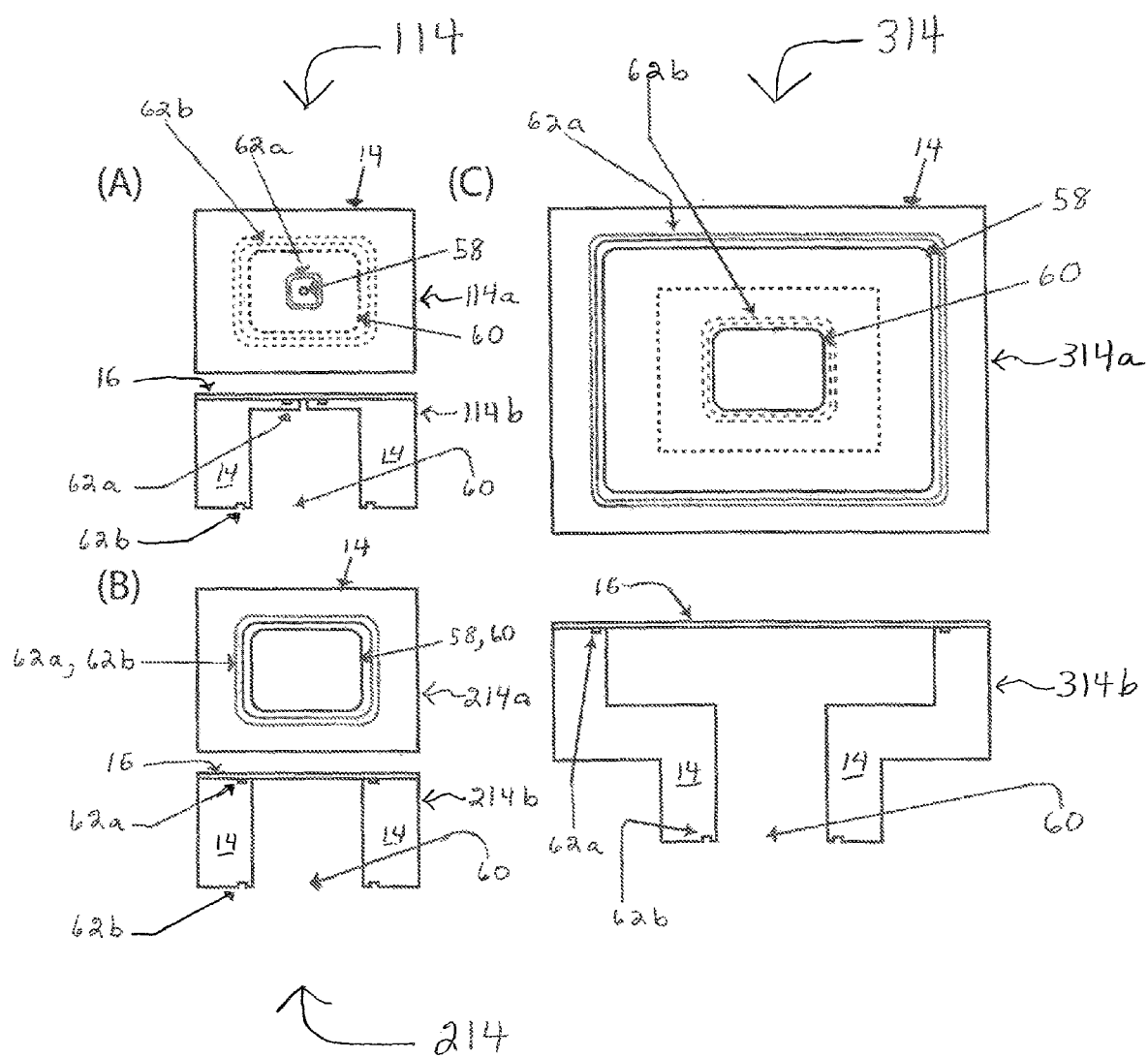
FIG. 7 A-C is a structural diagram of a top view and a sectioned side view of three exemplary spacer designs for accurately measuring barriers having different levels of permeability (high, medium and low).

The spacer may also be deployed with different size openings (or apertures) formed in the spacer, which define the measurement area of the barrier film. FIGS. 7A-C show exemplary embodiments 114, 214, and 314, respectively, of the spacer 14 having a barrier 16. FIG. 7A shows a top view 114a and side view 114b of the spacer 14, which may be used to test low permeability barrier materials. In this embodiment, an aperture 58 is shown opposite an opening 60 having a ratio less than one to one. FIG. 7B shows a top view 214a and side view 214b of the spacer 14, which may be used to test medium permeability barrier materials. In this embodiment, an aperture 58 is shown opposite an opening 60 having a ratio of about 1 to 1. FIG. 7C shows a top view 314a and side view 314b of the spacer 14, which may be used to test medium permeability barrier materials. In this embodiment, an aperture 58 is shown opposite an opening 60 having a ratio greater than one to one. The test card is not shown in these embodiments for simplicity. For purposes of illustration each of the spacers in FIGS. 7 A, B, and C is illustrated as proportionally dimensioned to mate with a 2 inch square test card. The barrier test device of FIG. 1 utilizes a FIG. 7 B spacer design.

The ratio of the aperture 58 of the spacer (which defines the barrier measurement area) to the opposite opening 60 of the spacer (which defines the calcium sensor area on the test card) helps determine the ultimate sensitivity. Reducing the aperture 58 area of the spacer supporting the barrier film 16 in relation to the opposite opening 60 in the spacer (as shown in 114 a and 114b of FIG. 7) enables water permeation measurements of materials with very high permeation rates. Maintaining the aperture 58 supporting the barrier 16 to the same size as the opposite opening 60 in the spacer as shown in 214a and 214b of FIG. 7) enables water permeation measurements of materials with medium permeation rates. Making a very large aperture 58 by expanding the spacer opening 60 supporting the barrier 16 while restricting the opening of the spacer in contact with the test card (as shown in 314a and 314b) results in higher sensitivity. High permeability barrier materials may be tested with aperture to opposite opening ratios of less than one to one (e.g. 0.01:1 or 0.1:1 or 0.5:1, etc.). Low permeability materials may be tested with aperture to opposite opening ratios of greater than one to one (e.g. 2:1 or 3:1 or 4:1, etc.). Medium permeability materials may be tested with an aperture to opposite opening ratio of about 1 to 1.

The use of trenches 62a and 62b in the spacer increases the reproducibility of the edge seal width. Under compression during the assembly of the test device, the edge sealant flows until it escapes from the region directly between the spacer and barrier 16 and between the spacer and the test card. This enables reproducibility of the size of the measurement area of the barrier in the aperture area as well as the opposite end contacting the test card. A trench 62a around the aperture 58 defining the barrier measurement area as shown in 114a, 214a and 314a of FIG. 7 allows for capturing the excesses of edge seal material and improves assembly by making more reproducible areas of barrier measurement. Cut-away side views of the trenches 62a and 62b in both the top and bottom of the spacer (respectively) are shown in the three exemplary spacer designs of 114 b, 214b, and 314b of FIG. 7. Any excess edge seal material may be compressed to flow into these trenches. If an edge seal with a desiccant is used, any flow of the edge seal into the measurement volume deleteriously can affect the measurement. While reproducible assembly techniques can result in a systematic offset, the spacer design can also be used to minimize edge seal overflow error, again by employing a trench on both the top 62a and bottom 62b of the spacer as shown in FIG. 7 A-C. However, it should be noted that although a trench offers several advantages, trenches in the spacer are not explicitly required.

The dimensions of the spacer are determined by a series of parameters. The width of the contact between the spacer and the barrier under test, as well as the contact with the test card, may be used to determine the width of the edge seal (or in the case of a spacer with a trench, the spacer edge is effectively defined by the trench). This minimum width may be determined by the desired testing duration, edge seal material, and determination whether (and how) to use a witness line.

In one example, this contact is typically at least about 10 mm wide for a test device employing a two inch square test card. This width reduces or altogether prevents moisture ingress at 85 C and 85% RH for more than 3000 hr. The edge seal width should account for the placement the witness line relative to the edge of the test card. For shorter tests, a more narrow edge seal may be used, permitting use of less bulky spacers and smaller test cards. Permeation tests of barriers requiring extended durations of time may require the use of a wider edge seal.

The height of the spacer, which defines the separation distance between the barrier and Ca sensor, may also be varied. In one example, the spacer may be sufficiently tall such that if a defect occurs at any point at the aperture, diffusion processes effectively normalize the defect(s) across all the Ca sensing area. A typical spacer height for separating a barrier and a two inch square test card may be on the order of one inch to normalize defects. Numerical modeling of the three-dimensional diffusion equation may be used to evaluate the effect of different locations of defects (sources) and Ca traces (sinks) for different spacer heights and Ca trace placement relative to spacer walls. As a general guide, the separation between the barrier and the Ca sensor may be of the same order of magnitude as the Ca sensor's largest dimension. In one example, the Ca traces are typically in an approximate 0.5×0.5 inch square at the center of the spacer, the inside of spacer's walls are between about 0.85 and 1 inch, and the height of the spacer is about 1 inch.

Assembly of the various components into an integrated test device is relatively straightforward. The edge sealant used to seal the components of the test device may be any suitable low-permeability adhesive (e.g., epoxies, ionomers, PIB-based sealants, etc.) For solid-film edge seals that are adherent (e.g. PIB-based edge seal tape), prior to assembly the edge seal may be applied directly to both ends of the spacers and allowed to outgas on a hotplate overnight in an inert environment (about 16 hours at about 120-140° C.). If a spacer is allowed to cool before assembly, the edge seal may absorb gas, which can result in bubbles in the final assembly. Alternatively, the edge seal material may be allowed to outgas separately from the spacer, and the full layer-by-layer assembly may be done immediately before use (e.g., in the case of liquid or non-adherent solid-film edge sealants).

To assemble a device with solid-film edge seals, the test device may be placed under compression (e.g., clamped) between two plates while heated (at about 50-140° C.) in an inert environment (e.g., placed in a glove box with oxygen and moisture levels typically less than about 1 ppm). Sufficient compression of the edge sealant is achieved by carefully tightening screws to achieve light pressure around the periphery of the plates in a balanced manner. A vacuum, hydraulic press, or other compression-type system may also be used to apply uniform pressure in compressing the edge seal.

The fully assembled and sealed test device is then ready for deployment in a controlled test environment to electrically measure the permeation characteristics of the barrier layer (e.g., steady state WTVRs as well as transients to determine breakthrough and lag times). A transient in this case is the change between zero permeation and the steady state level. Analysis of these non-steady state parts of the data allows one to extract additional information about a material. Environmental conditions for testing are typically exposure of the test device to air with elevated temperature and relative humidity. Test cards are designed to easily mate with readily commercially available edge card connectors that have been demonstrated to withstand 1000's of hours of exposure to damp heat (85 C and 85% RH). Other electrical connection methods may be readily envisioned.

The test device may be used by placing the test device in a controlled environment chamber, where the amount of oxidized Ca present (or alternatively, the amount of Ca missing) is detected by electrical means. The electronic detection method depends on the transition of the Ca film from a highly conductive metal to a non-conductive oxide. The amount of Ca remaining can be calculated from resistance measurements (using an assumed bulk resistivity for Ca), and the WVTR can be calculated from the rate of change in conductance with time.

Analyses of resistance data shows that the test device offers highly accurate and quantitative results. Degradation of the edge seal (and consequent termination of the measurement of the barrier film) is monitored by electrical resistance measurements as well. Using the test device under various environmental conditions, the electrical calcium test device displays excellent sensitivity for measuring steady state WTVRs ($10^{-6}$ g/m$^2$/day), as well as transients to determine breakthrough and lag times of barrier materials.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

The invention claimed is:

1. An electrical calcium test device for measuring permeability of a barrier material, comprising:
   a test card including a thin-film pattern of sensor metal deposited onto a substrate;
   an impermeable spacer having therein a volume of space defined by an interior wall of the impermeable spacer, wherein the volume of space traverses the impermeable spacer from a first aperture to a second aperture and separates the sensor metal from a test barrier material;
   a first edge seal which seals the test card to the impermeable spacer, and
   a second edge seal configured to seal the impermeable spacer to the test barrier material.

2. The device of claim 1, wherein the thin-film pattern includes a plurality of calcium (Ca) sensor lines connected on each side to inert electrically conductive lines extending to an edge of the test card.

3. The device of claim 2, wherein at least one of the plurality of Ca sensors is positioned external to the volume of space and between the first edge seal and the test card.

4. The device of claim 2, wherein at least one of the plurality of Ca sensors has a different line width than a second of the plurality of Ca sensors.

5. The device of claim 2, wherein at least one of the plurality of Ca sensors has enlarged contact pads at each end.

6. The device of claim 2, further comprising inert electrical lines contacting the plurality of Ca sensors so that resistance of the Ca sensors is measured in either a two- or four-point configuration.

7. The device of claim 6, wherein the inert electrical lines include one or both of platinum (Pt) or gold (Au), or alternatively include fluorine doped tin-oxide (F:SnO$_2$), indium zinc oxide (IZO), or indium tin oxide (ITO).

8. The device of claim 1, wherein the thin-film pattern of sensor metal is provided on an insulating substrate to form the test card.

9. The device of claim 1, wherein the thin-film pattern of sensor metal is deposited by sputtering and evaporation using a shadow mask technique.

10. The device of claim 1, wherein the interior wall of the impermeable spacer is a non-moisture absorbing wall comprising one or both of an out-gassed aluminum or an out-gassed silica.

11. The device of claim 1, wherein the impermeable spacer is comprised of at least one of metal, glass, or ceramic.

12. The device of claim 1, wherein the volume of space traverses the impermeable spacer from a first aperture that defines a barrier material measurement area to a second aperture that opens to the sensor metal and that defines a calcium sensor area.

13. The device of claim 12, wherein the first aperture is smaller than the second aperture.

14. The device of claim 12, wherein the second aperture is smaller than the first aperture.

15. The device of claim 1, wherein the impermeable spacer further comprises a trench positioned to receive sealant material.

16. The device of claim 1, wherein the impermeable spacer exhibits a height of one inch for separating a barrier from about a two inch square test card and a 0.5 inch wide edge seal.

17. The device of claim 12, wherein the impermeable spacer separates the sensor metal from the test barrier material such that diffusion normalizes moisture from a defect in the test barrier material across the calcium sensor area.

18. The device of claim 1, wherein one of both of the first edge seal and the second edge seal comprises a poly-isobutylene (PIB)-based material filled with desiccant.

19. The device of claim 18, wherein the PIB-based edge seal is applied directly to both ends of the impermeable spacer and allowed to outgas in a heated inert environment for 16 hours at 120-140° C. prior to assembly of the test device.

20. The device of claim 1 wherein the impermeable spacer and the second edge seal are sized for the thin-film pattern of sensor metal to contact an electrical connector extending to an edge of the test card.

21. The device of claim 1, further comprising a temperature sensing device integrated into the test card.

* * * * *